United States Patent [19]

Hamanaka

[11] Patent Number: 4,595,539
[45] Date of Patent: Jun. 17, 1986

[54] PREPARATION OF PENEM DERIVATIVES AND AZETIDINONE INTERMEDIATES

[75] Inventor: Ernest S. Hamanaka, Gales Ferry, Conn.

[73] Assignee: Pfizer Inc., New York, N.Y.

[21] Appl. No.: 502,894

[22] Filed: Jun. 10, 1983

[51] Int. Cl.⁴ .................. C07D 205/08; C07D 498/04; C07D 403/12; C07D 401/12

[52] U.S. Cl. ........................ 260/239 A; 544/364; 544/368; 260/245.2 R; 544/405; 544/406; 260/245.4; 544/407; 544/408; 260/330.3; 546/193; 546/194; 260/330.9; 546/198; 546/208; 544/3; 546/256; 546/270; 544/54; 546/275; 560/186; 544/58.2; 544/58.4; 544/58.5; 544/58.6; 544/58.7; 544/63; 544/96; 544/98; 544/111; 544/238; 544/310; 544/312; 544/316; 544/317; 544/319; 544/320; 544/321; 544/322; 544/326; 544/328; 544/331; 544/332; 544/333; 544/335; 544/336; 544/359

[58] Field of Search ............. 260/239 A, 245.4, 330.3, 260/330.9; 544/3, 54, 58.2, 58.4, 58.5, 58.6, 58.7, 63, 96, 98, 111, 238, 310, 312, 316, 317, 319, 320, 321, 322, 326, 328, 331, 332, 333, 335, 336, 359, 364, 368, 405, 406, 407, 408; 546/193, 194, 198, 208, 256, 270, 275

[56] References Cited

U.S. PATENT DOCUMENTS

| 3,668,201 | 6/1972 | Gutanski | 260/239.1 |
|---|---|---|---|
| 3,960,940 | 6/1976 | Elks | 260/534 S |
| 4,008,229 | 2/1977 | Spitzer | 260/239.1 |
| 4,020,077 | 4/1977 | Cook | 260/239.1 |
| 4,155,912 | 5/1979 | Menard et al. | 260/306.7 |
| 4,168,314 | 9/1979 | Christensen et al. | 424/270 |
| 4,207,323 | 6/1980 | Beattie et al. | 424/270 |
| 4,272,437 | 6/1981 | Menard et al. | 260/239 A |
| 4,290,948 | 9/1981 | Brain et al. | 260/245.2 |

FOREIGN PATENT DOCUMENTS

| 866845 | 9/1978 | Belgium . |
| 881012 | 1/1979 | Belgium . |
| 887886 | 3/1980 | Belgium . |
| 636 | 1/1979 | European Pat. Off. . |
| 2210 | 6/1979 | European Pat. Off. . |
| 58317 | 2/1981 | European Pat. Off. . |
| 70204 | 7/1981 | European Pat. Off. . |
| 51813 | 5/1982 | European Pat. Off. . |
| 69377 | 1/1983 | European Pat. Off. . |
| 91576 | 10/1983 | European Pat. Off. . |
| 66695 | 3/1979 | Japan . |
| 7176988 | 4/1981 | Japan . |
| 7197280 | 5/1981 | Japan . |
| 7200392 | 6/1981 | Japan . |
| 7200394 | 6/1981 | Japan . |
| 2013674 | 2/1978 | United Kingdom . |

OTHER PUBLICATIONS

Reese et al, "Protective Groups in Organic Chemistry" (pp. 95-142) 1973.
Haines, *Adv Carbohydrate Chain*, 33, 11-109 (1976).
Dininno, Journal of the American Chemical Society, 101,2210-11 (1979).
Oida et al., Tetrahedron Letters, 21,619-20 (1980).
Hayashi et al., 2-(Alkylthio)penem-3-Carboxylic Acids. V., *Chem. Pharm. Bull.*, 29(11), 3158-3172 (1981).
Yoshida et al., 2-(Alkylthio)penem-3-Carboxylic Acids. IV., *Chem. Pharm. Bull.*, 29(10), 2899-2909 (1981).
Volante, A, New Highly Efficient Method for the Conversion of Alcohols to Thioesters and Thiols, *Tetrahedron Letters*, 22(33), 3119-3122 (1981).
Oida et al., 2-(Alkylthio)penem-3-Carboxylic Acids. II., *Chem. Pharm. Bull.*, 28(11), 3258-3264 (1980).
DeNinno, et al., A Convenient Synthesis of Racemic 6-Hydroxyethyl-2-Alkylthio-Substituted Penems, *Tetrahedron Letters*, 28(35), 3535-38 (1982).
Tanaka et al., 2-Thioxopenams, Useful Intermediate for Penem Synthesis, *Chem. Comm.*, 1982(13), 713-714 (1982).
J. L. Wardell, Preparation of Thiols, in The Chemistry of the Thiol Group, S. Patai, ed., John Wiley & Sons, London, 1974, Chapt. 4.
A. Afonso et al., New Synthesis of Penems, the Oxamide Cyclization Reaction, *J. Amer. Chem. Soc.*, 104,6138-39 (1982).

*Primary Examiner*—Mark L. Berch
*Attorney, Agent, or Firm*—Charles J. Knuth; Albert E. Frost; Peter C. Richardson

[57] ABSTRACT

Certain 2-substituted-2-penem-3-carboxylic acid compounds and pharmaceutically-acceptable salts thereof can be prepared from the appropriate xanthate or trithiocarbonate by desulfurization and addition of an electrophilic sulfur compound followed by halogenation and ring closure. The corresponding desulfurized and halogenated olefinic intermediates are disclosed.

10 Claims, No Drawings

PREPARATION OF PENEM DERIVATIVES AND AZETIDINONE INTERMEDIATES

BACKGROUND OF THE INVENTION

This invention is directed to the preparation of a family of antibacterial agents incorporating a 2-azetidinone (beta-lactam) ring. Chemically, the antibacterial agents of this invention are identified as 2-substituted-2-penem-3-carboxylic acid compounds.

2-Substituted-2-penem-3-carboxylic acid compounds have been disclosed in U.S. Pat. No. 4,155,912; Belgian Pat. No. 866,845; published European patent application Nos. 636 and 2,210; and *Journal of the American Chemical Society*, 101, 2210 (1979). According to the abstract thereof published by Derwent Publications Ltd., published Japanese patent application No. 66694/1979 also discloses 2-substituted-2-penem-3-carboxylic acid compounds.

SUMMARY OF THE INVENTION

The present invention is directed to a method for the preparation of a compound of the formula $$\text{I}$$

or a pharmaceutically acceptable salt thereof, wherein:

R is hydrogen, 1-hydroxyalkyl having 1 or 2 carbon atoms or wherein the 1-hydroxyalkyl is substituted with a hydroxyl-protecting group;

$R_1$ is (alk)-G, (alk)-$G_1$, $G_1$ or $CH(G_2)_2$ wherein (alk) is an alkyl group having one to four carbon atoms;

G is hydrogen, alkoxy having one to five carbon atoms, 2-(alkoxy)ethoxy having three to seven carbon atoms, alkylthio having one to five carbon atoms, phenoxy, thiophenoxy, azido, amino, N-phenyl-N-alkylamino wherein the alkyl has one to four carbon atoms, N-alkanoylamino having two to six carbon atoms, N-(alkoxyalkanoyl)amino having three to ten carbon atoms, 2-(N-alkanoylamino)ethoxy having four to eight carbon atoms, aminocarbonyl, aminocarbonyloxy, N-alkylaminocarbonylamino having two to five carbon atoms, alkanoylaminoacetylamino having four to seven carbon atoms, N-alkylaminocarbonyloxy, aminocarbonylalkoxy having two to five carbon atoms, N-alkylaminocarbonyl having two to five carbon atoms, N-(alkoxyalkyl)aminocarbonyl having three to nine carbon atoms;

$G_1$ is azetidinyl or azetidinyl substituted with N-alkanoyl having two to six carbon atoms or an amine-protecting group; a five- or six-membered ring which is carbocyclic or heterocyclic having one or two oxygen atoms, one, two, three or four nitrogen atoms, a sulfur atom, a nitrogen atom and an oxygen atom or a nitrogen atom and a sulfur atom, or said five- or six-membered ring substituted with alkyl having one to four carbon atoms, dialkyl each having one to four carbon atoms, oxo, amino, amino substituted with an amine-protecting group, di(alkoxycarbonyl) each having two to five carbon atoms, alkoxycarbonyl having two to five carbon atoms, N-alkylaminocarbonyl having two to five carbon atoms, alkoxyalkyl having two to seven carbon atoms, phenyl, formyl, aminocarbonyl, N-alkylaminocarbonylamino having two to five carbon atoms, alkanoylamino having two to five carbon atoms, alkoxy having one to four carbon atoms or phenoxyacetyl;

$G_2$ is alkanoylaminomethyl each having three to seven carbon atoms or alkoxy each having one to four carbon atoms.

$R_2$ is hydrogen, an ester group which is hydrolyzed in vivo or a carboxylic acid protecting group; and X is oxygen or sulfur;

wherein the compound is prepared by the steps of:

(a) desulfurizing a first beta lactam of the formula $$\text{VI}$$

followed by the addition of an electrophile of the formula $R_6$—W to obtain a first olefin of the formula $$\text{VIII}$$

wherein:

$R_4$ is alkyl having 1–7 carbon atoms or alkyl substituted with alkoxy having 1–4 carbon atoms, phenyl, pyridyl or 2-benzothiazolyl;

i is zero or 1;

$R_6$ is a sulfur protecting group; and

W is a displaceable leaving group;

(b) halogenating said first olefin to obtain a second olefin of the formula $$\text{IV}$$

wherein $R_5$ is chloro, bromo or iodo; and (c) cyclizing the second olefin, to obtain said compound.

The hydroxyl-protecting group of R may be benzyloxycarbonyl, p-nitrobenzyloxycarbonyl, allyloxycarbonyl, 2,2,2-trichloroethoxycarbonyl or trialkylsilyl wherein each alkyl has 1–6 carbon atoms. When the hydroxyl-protecting group is trialkylsilyl, the method may include the additional step of removing the hydroxy-protecting group with a tetralkylammonium compound wherein each alkyl has one to seven carbon atoms; preferably the compound is a fluoride.

The carboxylic acid protecting group may be benzyl, p-nitrobenzyl, allyl or 2,2,2-trichloroethyl.

The amine protecting group may be benzyloxycarbonyl, p-nitrobenzyloxycarbonyl, allyloxycarbonyl, 2,2,2-trichloroethoxycarbonyl or, together with the amine nitrogen atom being protected, azido.

The method can include the additional step of removing the hydroxy-protecting group, carboxyl-protecting group or amine-protecting group by an appropriate method such as hydrogenation, treatment with zinc or treatment with tetrakis(triphenylphosphine)palladium.

$R_6$ can be alkanoyl having 2 to 8 carbon atoms, optionally substituted with alkoxy having 1 to 4 carbon atoms, phenyl, pyridyl or 2-benzothiazolyl.

Step (a) may employ a base or a base and a trivalent phosphorus compound. Preferably the base is sodium hydride. The trivalent phosphorus compound can be trialkylphosphine, triarylphosphine, or trialkylphosphite, preferably triphenylphosphine.

W may be chloro, bromo, iodo, alkanoyloxy having 2 to 8 carbon atoms, p-toluenesulfonate or alkyl-sulfonate having 1 to 4 carbon atoms. W is preferably chloro.

Step (c) employs a base, tetra-alkylammonium hydroxide wherein each alkyl has 1 to 7 carbon atoms, preferably tetra-n-butyl-ammonium.

Preferred is the method wherein R is hydrogen, X is sulfur and $R_1$ is methyl, ethyl, n-propyl, 2-methoxyethyl, 2-ethoxyethyl, 1-methoxy-2-propyl, 2,2-diethoxyethyl, 3-phenylpropyl, 2-(acetylamino)ethyl, 3-tetrahydrofuranyl, 2-tetrahydrofuranylmethyl, 2-(2-furanoylamino)ethyl, 1,3-dioxolan-2-ylmethyl, 2-(2-pyrrolidon-1-yl)ethyl, 2-(4-methylthiazol-5-yl)ethyl, 2-(2-pyridyl)ethyl, 2-aminoethyl or 2-(p-nitrobenzyloxycarbonylamino)ethyl; preferably wherein $R_2$ is p-nitrobenzyl.

The ester group of $R_2$ which is readily hydrolyzed in vivo may be alkanoyloxymethyl having from 3 to 8 carbon atoms, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-[alkoxycarbonyl]amino)ethyl having from 4 to 10 carbon atoms, 3-phthalidyl, 4-crotonolactonyl or gamma-butyrolacton-4-yl. Another class of esters which readily hydrolyze in vivo are the carboxyalkylcarbonyloxymethyl esters having from 4 to 12 carbon atoms.

Also embraced in the present invention are the first olefin (VIII) and second olefin (IV) as shown above. The substituents previously discussed apply to these olefins.

DETAILED DESCRIPTION OF THE INVENTION

The compounds of formula I are useful as antibacterial agents, or precursors thereof, and are derivatives of the bicyclic nucleus of the formula:

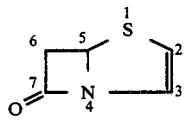
II

Throughout this specification, the nucleus of formula II is identified by the name "2-penem," and ring atoms are numbered as shown. Also, throughout this specification, the abbreviation "PNB" is used for the p-nitrobenzyl group.

When R is other than hydrogen, the relationship between the hydrogen on bridgehead carbon 5 and the remaining hydrogen on carbon 6 can either be cis or trans. The present invention embraces both isomers as well as mixtures thereof. The trans isomer is generally preferred in pharmaceutical applications and the cis isomer can be readily converted to the trans-isomer.

As will be appreciated various optically active isomers may exist. The present invention embraces such optically active isomers as well as mixtures thereof.

An ester group which readily hydrolyzes in vivo is intended to refer to non-toxic ester residues which are rapidly cleaved in mammalian blood or tissue to release the corresponding free acid (i.e., the compound of formula I wherein $R_2$ is hydrogen. Typical examples of such readily hydrolyzable ester-forming residues which can be used for $R_2$ are alkanoyloxymethyl having from 3 to 8 carbon atoms, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-[alkoxycarbonyl]amino)ethyl having from 4 to 10 carbon atoms, 3-phthalidyl, 4-crotonolactonyl and gamma-butyrolacton-4-yl. See U.S. Pat. No. 4,234,579 for further discussion. Another class of esters which hydrolyze readily in vivo are the carboxyalkylcarbonyloxymethyl esters having from 4 to 12 carbon atoms; a pharmaceutically acceptable cation may be employed with these esters.

The manner in which the compounds of formula I can be prepared is illustrated by reference to Scheme A. The compounds of formula I are obtained from the corresponding compound of formula IV. $R_1$ represents all of the same groups enumerated earlier except those groups which contain a primary or secondary amino group. When $R_1$ contains such an amino group, this is a special case which will be discussed hereinafter.

Scheme A

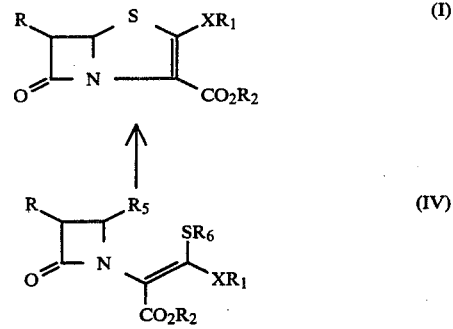

The compounds of formula I are obtained by cyclization of the corresponding compound of formula IV as shown in Scheme A. The cyclization is normally carried out by treatment of the compound of formula IV with a base, for example tetralkylammonium hydroxide, wherein each alkyl has 1 to 7 carbon atoms, in a two phase solvent system comprised of water and a water-immiscible solvent such as dichloromethane, at a pH of about 10.5. The reaction is normally carried out at a temperature range of about 5° to 35° C., preferably about 25° C. and it is normally complete within a few hours, e.g. from 2 to 24 hours. At the end of the cyclization reaction, the aqueous phase is separated and the product is recovered, for example, by solvent evaporation of the organic phase.

The manner in which the compounds of formula IV are obtained is illustrated by reference to Scheme B. According to the invention, these compounds are obtained by halogenation, preferably chlorination, of a compound of formula VIII.

A compound of formula VIII is preferably chlorinated with N-chlorosuccinimide if i is zero or oxalyl dichloride if i is one. When N-chlorosuccinimide is employed, an inert solvent such as dichloromethane is employed. The reaction is carried out at a temperature range of about $-30°$ to $10°$ C., preferably about $0°$ C.

If oxalyl dichloride is employed, a reaction-inert solvent such as dichloromethane is employed. The reaction is carried out at a temperature range of about $-40°$ to $10°$ C., preferably about $-20°$ C.

Conversion of VIII (i is zero) to VIII (i is one) can be readily carried out with an oxidizing agent such as a periodate such as sodium periodate or, preferably, m-chloroperbenzoic acid. Oxidation with m-chloroperbenzoic acid is generally carried out with a reaction-inert solvent such as dichloromethane at a temperature of between about $-20°$ and $10°$ C., preferably about $0°$ C.

Other suitable chlorinating reagents may also be employed. Furthermore $R_5$ need not be chloro in order for the conversion of IV to I to occur. Other halogens, e.g., bromo or iodo may be employed. These other halogens may be prepared by appropriate halogenation of VIII; for example, bromination with N-bromosuccinimide. Of course, $R_5$ may be any other suitable leaving group which will allow cyclization of IV to occur.

SCHEME B

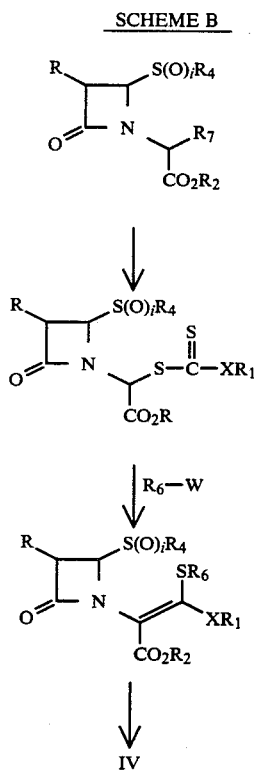

The compounds of formula VIII are obtained by desulfurization of a xanthate or trithiocarbonate of formula VI. The desulfurization is normally carried out by treating the compound of formula VI with about one molar equivalent of a strong base such as sodium hydride in a reaction-inert solvent such as tetrahydrofuran, at a temperature in the range of between about $-10°$ and $5°$ C., preferably about $0°$ C., followed by addition, in situ, of a compound of formula $R_6$—W. $R_6$ is a sulfur-protecting group such as alkanoyl having 2 to 8 carbon atoms, optionally substituted with alkoxy having 1 to 4 carbon atoms, phenyl, pyridyl or 2-benzothiazolyl. $R_6$ is preferably acetyl. The reaction is quenched by the addition of about one molar equivalent of acetic acid. The product is then recovered by solvent evaporation. Although the product thus obtained can be used directly in the preparation of a compound of formula IV, it is usual to purify VIII. Purification can be achieved by standard techniques; a particularly convenient method is chromatography on silica gel.

In some instances, in the conversion of a compound of the formula VI into a compound of formula VIII, it is advantageous to add one molar equivalent of a trivalent phosphorus compound such as a trialkylphosphine (e.g., tributylphosphine, tricyclohexylphosphine), a triarylphosphine (e.g., triphenylphosphine) or a trialkylphosphite (e.g., trimethylphosphite, triethylphosphite), preferably triphenylphosphine, to the reaction medium prior to the addition of the strong base.

W is a leaving group which can be displaced by X under the reaction conditions. For example, W can be chloro, bromo, iodo, alkanoyloxy having 2-5 carbon atoms, p-toluenesulfonate, methylsulfonate and the like, preferably chloro.

The compounds of formula VI are obtained by coupling the compound of the formula V with a xanthate salt of the formula $M^+R_1$—O—(C=S)—S$^-$, or a trithiocarbonate salt of the formula $M^+R_1$—S—(C=S)S, wherein $M^+$ represents a metal cation such as sodium or potassium. $R_7$ is a group displacable by a xanthate or trithiocarbonate group such as halo group(chloro, bromo or iodo). The coupling is normally carried out by contacting equimolar amounts of the xanthate salt or trithiocarbonate salt and the compound of formula V in a biphasic organic-aqueous mixture such as dichloromethane and water, in the presence of one molar equivalent or less of a phase-transfer catalyst such as benzyltriethylammonium chloride. The reaction is normally carried at a temperature between about $0°$ and $30°$ C., preferably about $0°$ C., and it is usually complete within one to two hours. At the completion of the reaction, the product is in the organic phase, and it can be recovered by separating the layers and evaporating the solvent. The product can be purified by conventional methods for a beta-lactam compound, e.g. chromatography using silica gel.

The method by which the compound of formula V can be prepared is shown in Scheme C. Thus, it will be seen that the compound of formula V is prepared by halogenation of the corresponding hydroxy compound (XIII) with a chlorinating or brominating agent such as thionyl chloride, methanesulfonyl chloride, or methanesulfonyl bromide. For thionyl chloride, the chlorination is carried out by treating a solution of the compound of formula XIII in tetrahydrofuran with a slight molar excess of thionyl chloride, in the presence of a hindered amine such as 2,6-lutidine, at about $0°$ C. Reaction takes place rapidly, and after about 15 minutes, the product is recovered by evaporation of the filtered tetrahydrofuran solution.

SCHEME C

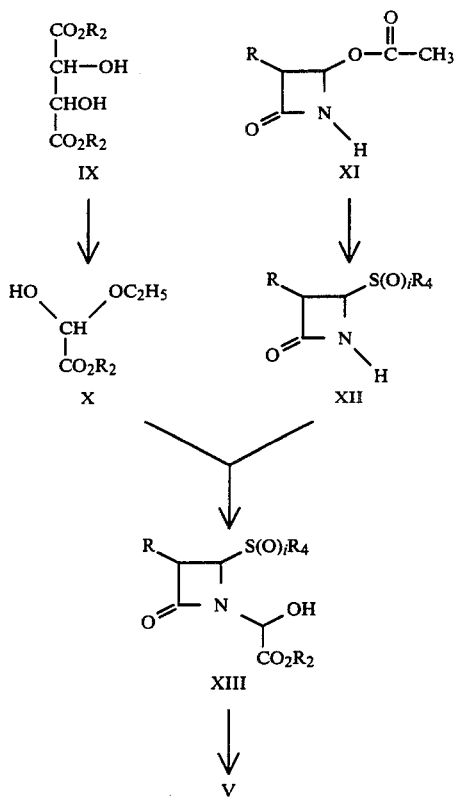

SCHEME D

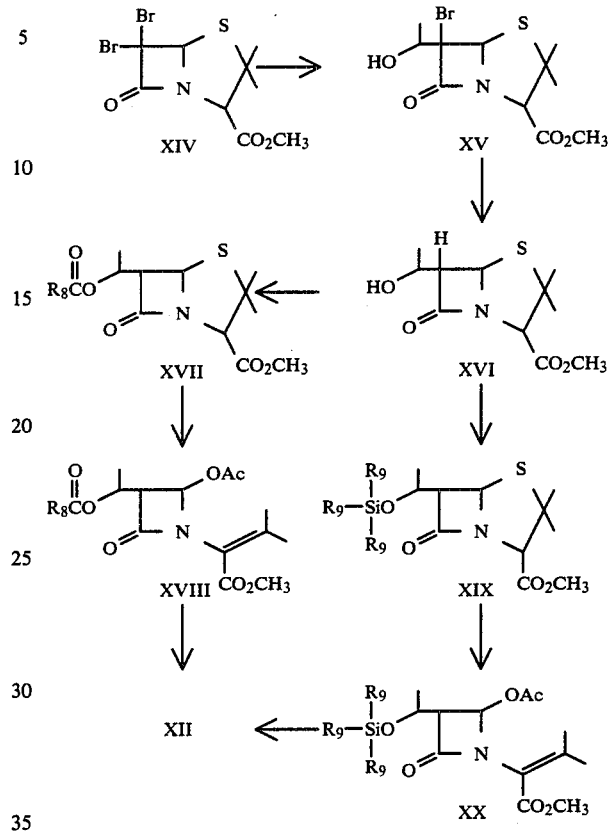

The compound of formula XIII is prepared by coupling a compound of formula XII with the ester of glyoxylic acid ethyl hemiacetal (X). The coupling is carried out by heating the two reagents in refluxing benzene, with provision for continuous removal of water and ethanol by azeotropic distillation.

An alternate procedure is to treat XII (R is preferably 1-hydroxyethyl or hydroxymethyl having a hydroxyl-protecting group such as p-nitrobenzyloxycarbonyl) with a benzyloxycarbonylformaldehyde to obtain XIII ($R_2$=benzyl group). The preferred benzyloxycarbonylformaldehyde is p-nitro-benzyloxycarbonylformaldehyde which is reacted with XII in an aprotic solvent such as benzene or N,N-dimethylformamide, preferably benzene at a temperature of about 80° C.

The azetidine of formula XII is prepared from the corresponding 4-acetoxy-2-oxo-azetidine XI by reaction with the sodium salt of the thiol. $R_4$ is alkyl having 1–7 carbon atoms or alkyl substituted with alkoxy having 1–4 carbon atoms, phenyl, pyridyl or 2-benzothiazolyl. Of course other appropriate substituents known in the art may also be employed. Likewise $R_4$ can be any group which can survive the subsequent reactions without interfering with them and yet be removed by halogenation or otherwise allow the subsequent cyclization to occur. The ester of glyoxylic acid ethyl hemiacetal X is prepared by periodic acid cleavage of the corresponding ester of tartaric acid IX. 4-Acetoxy-2-oxo-azetidines XI and the tartrates IX are prepared by methods known in the art. The sulfide (XII or XIII, i is zero) may be oxidized to the sulfoxide (i is one) by the previously-discussed methods.

As shown in Scheme D, when R is 1-hydroxyethyl or the hydroxyl protected form thereof, the compound of formula XII can be prepared from the known dibromo penam of formula XIV. The dibromo penam (XIV) undergoes an exchange reaction with t-butyl magnesium chloride at a temperature of between about −90° and −40° C., preferably about −76° C. in a reaction-inert solvent such as tetrahydrofuran, diethyl ether or toluene, preferably tetrahydrofuran. Other organometallic reagents may also be employed. The resulant reaction mixture is treated in situ with the appropriate aldehyde; acetaldehyde for the 1-hydroxyethyl derivative, formaldehyde for the hydroxymethyl derivative. The aldehyde is added at between about −80° and −60° C., preferably about −76° C. for acetaldehyde.

The resulting bromo hydroxy penam XV is hydrogenated to remove the 6-bromo substituent. A suitable hydrogenation catalyst is a noble metal catalyst such as palladium. The reaction is carried out in a protic solvent such as 1:1 methanol-water or 1:1 tetrahydrofuran-water, preferably 1:1 methanol-water, at a pressure of about 1 to 4 atms, preferably 4 atm and a temperature of between about 0° and 30° C., preferably about 25° C.

The hydrogenated compound XVI is treated to protect the hydroxyl with a hydroxyl-protecting group ($R_8CO$) such as benzyloxycarbonyl, p-nitrobenzyloxycarbonyl, allyloxycarbonyl, 2,2,2-trichloroethoxycarbonyl and the like. The hydroxyl is reacted, for example, with the corresponding chloride, bromide or iodide of the hydroxyl-protecting group. For p-nitrobenzyloxycarbonyl, the chloride is reacted with XVI in suitable reaction-inert solvent such as dichloromethane and the reaction is carried out at a temperature between about 0° and 30° C., preferably about 25° C.

The resulting alkanoyl penam XVII is treated with mercuric acetate in acetic acid at a temperature of about 90° C. to yield the olefin XVIII.

In order to obtain the desired azetidinone XII, the olefin XVIII is ozonized in a reaction-inert solvent such as dichloromethane at a temperature of between about −80 and −40, preferably about −76° C. The reaction product is not isolated, but is treated with an alkanol such as methanol to yield the azetidine XII.

Alternatively the alcohol of formula XVI can be protected with a trialkylhalosilane of formula

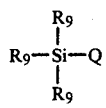

wherein $R_9$ at each occurrance is an alkyl of 1 to 6 carbon atoms and Q is chloro, bromo or iodo. Thus, dimethyl-t-butylchlorosilane in the presence of an amine proton acceptor such as imidazole in a polar, aprotic solvent such as N,N-dimethylformamide at a temperature range of between about 5° and 40° C., preferably about 25° C. forms a trialkylsilyl hydroxyl-protecting group as shown in formula XIX.

Mercuric acetate treatment of XIX under the conditions employed with XVII results in the olefin XX. Ozonolysis of this olefin XX in the same method employed with XVIII results in XII wherein R is the trialkylsilyl derivative of 1-hydroxylethyl or hydroxymethyl.

The xanthate salts of the formula $M^+R_1$—O—(C=S)—$S^-$ are prepared from the appropriate alcohol of formula $R_1$—OH and carbon disulfide in the presence of a strong base. For example, the alcohol of formula $R_1$—OH is reacted with an equimolar amount of sodium hydride or potassium t-butoxide, followed by a slight excess of carbon disulfide, according to well-known procedures.

The trithiocarbonate salts of the formula $M^+R_1$—S—(C=S)—$S^-$ are prepared from the appropriate mercaptan of the formula $R_1$—SH or by treatment of a thioacetate of the formula $R_1SC(O)CH_3$ with an alkaline metal alkoxide followed by carbon disulfide.

Conversion of a compound of formula I wherein $R_2$ is an acid protecting group into a compound of formula I wherein $R_2$ is hydrogen is accomplished using methods familiar to those in the art. For example, when $R_2$ is benzyl or p-nitrobenzyl the procedure used is a conventional hydrogenolysis reaction, and it is carried out in conventional fashion for this type of transformation. Thus, a solution of a compound of the formula I ($R_2$ is a carboxylic acid protecting group) is stirred or shaken under an atmosphere of hydrogen, or hydrogen mixed with an inert diluent such as nitrogen or argon, in the presence of a catalytic amount of a hydrogenolysis catalyst, such as a palladium-on-calcium carbonate catalyst. Convenient solvents for this hydrogenolysis are lower-alkanols, such as methanol; ethers, such as tetrahydrofuran and dioxan; low molecular weight esters, such as ethyl acetate and butyl acetate; water; and mixtures of these solvents. However, it is usual to choose conditions under which the starting material is soluble. The hydrogenolysis is usually carried out at room temperature and at a pressure from about 0.5 to about 5 kg/cm². The catalyst is usually present in an amount from about 10 percent by weight based on the starting material up to an amount equal in weight to the starting material, although larger amounts can be used. The reaction commonly takes about one hour, after which the compound of the formula I ($R_2$ is hydrogen), is recovered simply by filtration followed by removal of the solvent in vacuo. If palladium-on-calcium carbonate is used as the catalyst, the product is often isolated as the calcium salt. The compounds of formula I can be purified by conventional methods for beta-lactam compounds. For example, the compounds of Formula I can be purified by gel filtration on Sephadex, or by recrystallization.

If for I, R is 1-hydroxyethyl or hydroxymethyl protected with, for example, benzyl derivatives such as p-nitrobenzyloxycarbonyl, the hydroxyl-protecting group can be removed using the hydrogenolysis procedure just described.

For compounds of formula I wherein R is 1-hydroxyethyl or hydroxymethyl whose hydroxyl group is protected with a tialkylsilyl group, the trialkylsilyl group is preferably removed prior to the hydrogenolysis to remove the acid-protecting group (I, $R_2$ is an acid protecting group). The trialkylsilyl group is removed with a tetralkylammonium compound such as the fluoride, generally wherein each alkyl has 1 to 7 carbon atoms, such as tetra-n-butylammonium hydroxide in a ethereal solvent such as tetrahydrofuran at a temperature range of about 15° to 40° C., preferably about 25° C.

The compound of the formula I, wherein $R_1$ includes a primary amino group, can be prepared from the corresponding azido compound by hydrogenolysis. The conditions described earlier for removal from I of $R_2$ wherein $R_2$ is an acid protecting group such as the p-nitrobenzyl group can be used for this azido hydrogenolysis reaction, but it is necessary to allow the reaction to proceed until reaction with hydrogen ceases. Thus, it is evident that if one subjects the compound of formula I, wherein $R_1$ includes an azido group, to the aforesaid hydrogenolysis conditions, partial hydrogenolysis leads to the compound of formula I, wherein $R_1$ includes the azido group; exhaustive hydrogenolysis leads to the compound of formula I, wherein the azido group of $R_1$ has been converted to a primary amino group.

Alternatively, primary and secondary amines can be protected with suitable amine-protecting groups such as p-nitrobenzyloxycarbonyl benzyloxycarbonyl, allyloxycarbonyl 2,2,2-trichloroethoxycarbonyl and the like. The corresponding chloride, for example, p-nitrobenzyloxycarbonyl chloride, can be reacted with the amine in a reaction-inert solvent such as dichloromethane at a temperature range of about −20° to 25° C., preferably about 0° C. The amine-protecting group, such as p-nitrobenzyloxycarbonyl can be removed by the same hydrogenolysis procedure previously described.

The compounds of formula I are acidic and will form salts with basic agents. Such salts are considered to be within the scope of this invention. These salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions by lyophilization, as appropriate. Basic agents which are suitably employed in salt formation belong to both the organic and inorganic types, and they include ammonia, organic amines, alkyli metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4,3,0]-non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethylhexanoate.

Preferred salts of the compounds of formula I are sodium, potassium and calcium salts.

As indicated hereinbefore, the compounds of formula I and salts thereof are anti-bacterial agents. The in vitro activity of the compounds of the formula I and salts thereof can be demonstrated by measuring their minimum inhibitory concentrations (MIC's) in mcg/ml against a variety of microorganisms. The procedure which is followed is the one recommended by the International Collaborative Study on Antibiotic Sensitivity Testing (Ericcson and Sherris, *Acta. Pathologica et Microbiologia* Scandinav, Supp. 217, Section B: 64–68 [1971]), and employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hrs. at 37° C. The susceptibility (MIC) of the test organism is accepted as the lowest concentration of compound capable of producing complete inhibition of growth as judged by the naked eye.

The following Examples and Preparations are provided solely for further illustration. Infra-red (IR) spectra were measured either as potassium bromide discs (KBr disc), or as solutions in chloroform ($CHCl_3$), methylene chloride ($CH_2Cl_2$) or dimethyl sulfoxide (DMSO), and diagnostic absorption bands are reported in either microns or wave numbers ($cm^{-1}$). Nuclear magnetic resonance (NMR) spectra were measured for solutions in deuterochloroform ($CDCl_3$) or perdeuterodimethyl sulfoxide (DMSO-$d_6$), or mixtures thereof, and peak positions are expressed in parts per million downfield from tetramethylsilane. The following abbreviations for peak shapes are used: s, singlet; d, doublet; t, triplet; q, quartet; m, multiplet; b, broad; c, complex. The abbreviations "ss" and "sss" denote that a particular proton appeared as two or three singlets respectively, owing to the presence of diastereoisomers. Throughout the Examples and Preparations, the abbreviation "PNB" represents the p-nitrobenzyl group.

EXAMPLE 1 p-Nitrobenzyl 2-(4-ethylthio-2-oxo-1-azetidinyl)-3-acetylthio-3-(2-ethoxyethylthio)acrylate A solution of 2.3 g p-nitrobenzyl 2-(4-ethylthio-2-oxo-1-azetidinyl)-2-[2-ethoxyethylthio(thiocarbonyl)-thio]acetate and 1.19 g triphenylphosphine in 100 ml anhydrous tetrahydrofuran was cooled to 0° C. under a nitrogen atmosphere, sodium hydride (0.22 g as a 50% oil dispersion) was added and the mixture was stirred at 0° C. for 1 hour. Acetyl chloride (0.32 ml) was then added and the mixture was stirred at 0° C. for 30 minutes. The reaction mixture was then concentrated in vacuo and the residue was partitioned between chloroform (100 ml) and water (50 ml). The chloroform solution was separated, washed with two 50 ml portions of water, dried over anhydrous sodium sulfate and concentrated in vacuo to a semi-solid residue. The residue was chromatographed on silica gel impregnated with formamide (10% by weight). Elution with 10% ethyl acetate in chloroform yielded 1.42 g of the title compound. The NMR spectrum in deuterochloroform solution showed peaks at 1.2(m,6H); 2.3–3.76(C,13H); 5.07–5.66(C,3H); 7.56(m,2H); and 8.2(m,2H) ppm. The IR spectrum in dichloromethane solution had absorption bands at 5.65 and 5.78 microns.

EXAMPLE 2

The procedure of Example 1 was employed with the corresponding $R_1$ thio(thiocarbonyl)thio acetate of formula VI to obtain the corresponding product of formula VIII listed in Table I. In all cases R is hydrogen, $R_2$ is p-nitrobenzyl, X is sulfur, i is zero, $R_4$ is ethyl and $R_6$ is acetyl. IR spectra were measured for solutions as indicated and NMR spectra were measured for solutions in deuterochloroform.

TABLE I

| $R_1$ | IR (Microns) | NMR(ppm) |
|---|---|---|
| ethyl | 5.65 ($CHCl_3$) | 1.24(m, 6H); 2.18–3.66 (c, 9H); 5.04–5.7(c, 3H); 7.58(m, 2H); and 8.26 (m, 2H) |
| 3-phenylpropyl | 5.66 and 5.77 ($CHCl_3$) | 1.18(m, 3H; 2.0(m, 2H); 2.25 and 2.36(s, 3H); 2.4–3.62(c, 8H); 5.0–5.56(c, 3H); 7.24(m, 5H); 7.54(m, 2H); and 8.22 (m, 2H) |
| methyl | 5.62 and 5.77 ($CH_2Cl_2$) | 1.18(m, 3H); 2.24–3.66 (c, 10H); 5.1 and 5.5 (m, 1H); 5.32(d, 2H); 7.6(d, 2H); and 8.28 (d, 2H) |
| 2-(acetylamino) ethyl | 5.64, 5.78 and 5.98 ($CH_2Cl_2$) | 1.2(m, 3H); 1.96(s, 3H); 2.38 and 2.5(s) and 2.28–3.7(c, 11H); 5.08–5.54(c, 3H); 7.06(b, 1H); 7.6(m, 2H); and 8.22 (m, 2H) |
| 2-(methoxy)ethyl | 5.66 and 5.78 ($CHCl_3$) | 1.2(m, 3H); 2.32, 2.45 and 3.32(s) and 2.28–3.7 (c, 14H); 5.12 and 5.54 (m, 1H); 5.4(d, 2H); 7.56 (m, 2H); and 8.22(m, 2H) |
| propyl | 5.66 and 5.78 ($CHCl_3$) | 0.8–1.86(c, 8H); 2.36 and 2.46(s) and 2.32–3.8 (c, 9H); 5.04–5.64(c, 3H); 7.64(m, 2H); and 8.3 (m, 2H) |
| 2-(4-methyl-thiazol-5-yl) ethyl | 5.64 ($CHCl_3$) | 1.2(m, 3H); 2.26–3.7 (c, 14H); 5.06–5.55 (c, 3H); 7.58(m, 2H); 8.2(m, 2H); and 8.58 (s, 1H) |
| 1,3-dioxolan-2-ylmethyl | 5.64 and 5.78 ($CH_2Cl_2$) | 1.2(m, 3H); 2.0–4.02 (c, 3H); 4.9–5.62 (c, 4H); 7.52(m, 2H); and 8.18(m, 2H) |
| 2-(2-pyrrolidon-1-yl)ethyl | 5.66, 5.77 and 5.97 ($CHCl_3$) | 1.2(m, 3H); 1.66–3.68 (c, 17H); 4.94–5.6 (c, 3H); 7.54(m, 2H); |

TABLE I-continued

| R₁ | IR (Microns) | NMR(ppm) |
|---|---|---|
| 2-(2-furanoyl-amino)ethyl | 5.64, 5.82 and 6.02 (CH$_2$Cl$_2$) | and 8.2(m, 2H) 1.2(m, 3H); 2.2–3.8 (c, 11H); 4.7–5.55 (c, 3H); 6.44(m, 1H); 7.15(c, 1H); 7.26–7.77(c, 4H) and 8.2 (m, 2H) |
| 2,2-diethoxy-ethyl | 5.65 and 5.78 (CHCl$_3$) | 1.14(m, 9H); 2.14–3.8(c, 13H); 4.37–5.53(c, 4H); 7.4 (m, 2H); and 8.08 (m, 2H) |
| 2-(p-nitrobenzyl-oxycarbonyl-amino)ethyl | 5.64 and 5.8 (CH$_2$Cl$_2$) | 1.2(m, 3H); 2.28–3.7(c, 11H); 5.32 (c, 5H); 7.57(c, 5H); and 8.2(m, 4H) |
| 2-(2-pyridyl) ethyl | 5.6 and 5.77 (CH$_2$Cl$_2$) | 1.16(m, 3H); 2.3, 2.4(s) and 2.2–3.6(c, 11H); 5.22 (c, 3H); 7.08(m, 2H); 7.48(c, 3H); 8.12 (m, 2H) and 8.44 (m, 1H) |

EXAMPLE 3 p-Nitrobenzyl 2-(4-ethylsulfinyl-2-oxo-1-azetidinyl)-3-acetylthio-3-(2-ethoxyethylthio)acrylate A solution of 1.4 g p-nitrobenzyl 2-(4-ethylthio-2-oxo-1-azetidinyl)-3-acetylthio-3-(2-ethoxyethylthio)acrylate in 75 ml. methylene chloride was cooled to 0° C. under a nitrogen atmosphere. A solution of 0.551 g m-chloroperbenzoic acid in 25 ml methylene chloride was added dropwise, then the reaction mixture was stirred at 0° C. for 1 hour. The methylene chloride solution was then washed with two 25 ml portions of saturated aqueous sodium bicarbonate solution and two 25 ml portions of water, dried over anhydrous sodium sulfate and concentrated in vacuo to an oil. The crude title compound (1.25 g) was used without further purification. The NMR spectrum of a deuterochloroform solution showed peaks at 1.24(m,6H); 2.27–3.74(c,13H); 4.7–5.46(c,3H); 7.75(m,2H); and 8.23(m,2H) ppm. The infrared spectrum of a dichloromethane solution has absorption bands at 5.6 and 5.79 microns.

EXAMPLE 4

The procedures of Example 3 with compounds of formula VIII wherein R is hydrogen, R$_2$ is p-nitrobenzyl, R$_4$ is ethyl, X is sulfur, R$_6$ is acetyl and i is zero were used to obtain the corresponding compound of formula VIII wherein i is one, as shown in Table II. IR spectra were measured for solutions as indicated and NMR spectra were measured for solutions in deuterchloroform.

TABLE II

| R₁ | IR (Microns) | NMR(ppm) |
|---|---|---|
| ethyl | 5.62 (CH$_2$Cl$_2$) | 1.34(m, 6H); 2.3–3.7 (c, 9H); 5.1–5.6(c, 3H); 7.62(m, 2H); and 8.28 (m, 2H) |
| 3-phenylpropyl | 5.6 and 5.78 (CHCl$_3$) | 1.3(m, 3H); 2.0(m, 2H); 2.3 and 2.4(s, 3H); 2.5–3.9(c, 8H); 4.7–5.44(c, 3H); 7.28 (m, 5H); 7.6(m, 2H); and 8.22(m, 2H) |
| methyl | 5.6 and 5.78 (CH$_2$Cl$_2$) | 1.26(m, 3H); 2.2–3.7 (c, 10H); 4.7–5.27 (c, 3H); 7.52(m, 2H); and 8.2(m, 2H) |
| 2-(4-methyl-thiazol-5-yl) ethyl | 5.6 and 5.77 (CH$_2$Cl$_2$) | 1.3(m, 3H); 2.28–3.92 (c, 14H); 4.78–5.5 (c, 3H); 7.6(m, 2H); 8.2(m, 2H); and 8.6(s, 1H) |
| 1,3-dioxolan-2-ylmethyl | 5.6 and 5.77 (CH$_2$Cl$_2$) | 1.3(m, 3H); 2.12–4.0 (c, 13H); 4.66–5.36 (c, 4H); 7.5(m, 2H); and 8.2(m, 2H) |
| 2-(2-pyrrolidon-1-yl)ethyl | 5.6, 5.8 and 5.99 (CH$_2$Cl$_2$) | 1.26(m, 3H); 1.66–3.86(c, 17H); 4.66–5.43(c, 3H); 7.5 (m, 2H); and 8.2 (m, 2H) |
| 2-(2-furanoyl-amino)ethyl | 5.6, 5.78 and 6.03 (CH$_2$Cl$_2$) | 1.3(m, 3H); 2.2–3.98 (c, 11H); 4.74–5.43 (c, 3H); 6.46(m, 1H); 7.0–7.7(c, 5H); and 8.2(m, 2H) |
| 2,2-diethoxy-ethyl | 5.6 and 5.78 (CH$_2$Cl$_2$) | 1.2(m, 9H); 2.22–3.8 (c, 13H); 4.27–5.4 (c, 4H); 7.48(m, 2H); and 8.1(m, 2H) |
| 2-(p-nitro-benzyloxy-carbonylamino) ethyl | 5.55 and 5.74 (CH$_2$Cl$_2$) | 1.3(m, 3H); 2.28–3.8 (c, 11H); 4.8–5.6 (c, 5H); 7.54(c, 5H); and 8.2(m, 4H) |
| 2-(2-pyridyl) ethyl | 5.6 and 5.78 (CH$_2$Cl$_2$) | 1.3(m, 3H); 2.34, 2.46 (s) and 2.25–3.96 (c, 11H); 4.72–5.44 (c, 3H); 7.14(m, 2H); 7.6(c, 3H); 8.25 (m, 2H); and 8.56 (m, 1H) |

EXAMPLE 5 p-Nitrobenzyl 2-(4-chloro-2-oxo-1-azetidinyl)-3-acetylthio-3-(2-ethoxyethylthio)acrylate A solution of 1.2 g p-nitrobenzyl 2-(4-ethylsulfinyl-2-oxo-1-azetidinyl)-3-acetylthio-3-(2-ethoxyethylthio)-acrylate in 50 ml methylene chloride was cooled to −50° C. under a nitrogen atmosphere. Oxalyl chloride (0.196 ml) was added dropwise at −50° C., then the reaction mixture was allowed to warm to −15°. After 1 hour at −15° C. the methylene chloride solution was washed with 20 ml saturated aqueous sodium bicarbonate solution and 20 ml water, dried over anhydrous sodium sulfate and concentrated in vacuo to an oil (1.2 g). The crude title compound was used without further purification. The NMR spectrum of a deuterochloroform solution showed peaks at 1.23(m,3H); 2.3–3.72(c,11H); 5.23(m,2H); 5.7–6.32(c,1H); 7.52(m,2H); and 8.2(m,2H) ppm. The infrared spectrum of a chloroform solution had absorption bands at 5.6 and 5.78 microns.

EXAMPLE 6

The procedures of Example 5 were used with compounds of formula VIII wherein R is hydrogen, R$_2$ is p-nitrobenzyl, R$_4$ is ethyl, R$_6$ is acetyl, X is sulfur and i is one to obtain the corresponding compound of formula IV wherein R$_5$ is chloro and R$_1$ is as shown in Table III. IR spectra were measured for solutions in the solvent indicated and NMR spectra were measured for solutions in deuterochloroform.

TABLE III

| $R_1$ | IR (Microns) | NMR(ppm) |
|---|---|---|
| ethyl | 5.6 ($CH_2Cl_2$) | 1.3(m, 3H); 2.1–3.9 (c, 7H); 5.2(m, 2H); 5.84–6.4(c, 1H); 7.6(m, 2H); and 8.3(m, 2H) |
| 3-phenyl-propyl | 5.6 and 5.77 ($CHCl_3$) | 1.98(m, 2H); 2.28 and 2.32(s, 3H); 2.5–3.9 (c, 6H); 5.3(m, 2H); 5.9 and 6.2(m, 1H); 7.2(b, 5H); 7.52 (d, 2H); and 8.22 (d, 2H) |
| methyl | 5.6 and 5.77 ($CH_2Cl_2$) | 2.16, 2.22 and 2.5 (s, 6H); 2.9–3.9 (m, 2H); 5.32(d, 2H); 5.88 and 6.28 (m, 1H); 7.6(d, 2H); and 8.3(d, 2H) |
| 2-(4-methyl-thiazol-5-yl)ethyl | 5.6 and 5.78 ($CH_2Cl_2$) | 2.4(m, 6H); 2.9–3.66 (c, 6H); 5.34(m, 2H); 5.8–6.26(c, 1H); 7.6(m, 2H); 8.26 (m, 2H); and 8.66 (s, 1H) |
| 1,3-dioxolan-2-ylmethyl | 5.6 and 5.77 ($CH_2Cl_2$) | 2.04–4.08(c, 11H); 5.06(m, 1H); 5.3(m, 2H); 5.7–6.37(c, 1H); 7.54 (m, 2H); and 8.22(m, 2H) |
| 2-(2-pyrrolidon-1-yl)ethyl | 5.6, 5.77 and 5.96 ($CH_2Cl_2$) | 1.74–3.94(c, 15H); 5.34(m, 2H); 5.87–6.4 (c, 1H); 7.6(m, 2H); and 8.2(m, 2H) |
| 2-(2-furanoyl-amino)ethyl | 5.58, 5.76 and 6.02 ($CH_2Cl_2$) | 2.2–4.0(c, 9H); 5.36 (m, 2H); 5.88–6.34 (c, 1H); 6.46(m, 1H); and 7.03–8.4(c, 7H) |
| 2,2-diethoxy-ethyl | 5.6 and 5.79 ($CH_2Cl_2$) | 1.22(m, 6H); 2.28–4.4 (c, 12H); 5.24(m, 2H); 5.5–6.0(c, 1H); 7.5 (m, 2H); and 8.2(m, 2H) |
| 2-(p-nitro-benzyloxy-carbonyl-amino)ethyl | 5.6, 5.75 and 5.8 ($CH_2Cl_2$) | 2.16–3.8(c, 9H); 5.22 (m, 4H); 5.86, 6.08 (m, 1H); 7.5(c, 5H); and 8.16(m, 4H) |
| 2-(2-pyridyl)ethyl | 5.6 and 5.77 ($CH_2Cl_2$) | 2.36, 2.46(s, 3H); 2.9–3.88(c, 6H); 5.3(m, 2H); 5.8–6.25(c, 1H); 7.0–7.9(c, 5H); 8.2(d, 2H); and 8.54(m, 1H) |

EXAMPLE 7 p-Nitrobenzyl 2-(4-chloro-2-oxo-1-azetidinyl)-3-acetylthio-3-(2-methoxyethylthio)acrylate A solution of 1.8 g of 2-(4-ethylthio-2-oxo-1-azetidinyl)-3-acetylthio-3-(2-methoxyethylthio)acrylate in 100 ml dichloromethane was cooled to 0° C. and, while under a nitrogen atmosphere, 0.48 g N-chlorosuccinimide was added portionwise. The resulting solution was stirred at 0° C. for two hours, washed sequentially with 25 ml of a saturated aqueous sodium bicarbonate solution and two 25 ml portions of water, dried over anhydrous sodium sulfate and concentrated in vacuo to an oily product (1.8 g) which was the title compound and was used without further purification. The NMR solution spectrum in deuterochloroform showed peaks at 2.36 and 2.46(s,3H); 3.36(s) and 2.98–4.0(c,9H); 5.36(d,2H); 5.94 and 6.34(m,1H); 7.6(m,2H); and 8.24(m,2H) ppm. The infrared spectrum had absorption peaks at 5.6 and 5.78 microns for a chloroform solution.

EXAMPLE 8

The procedure of Example 7 were employed with compounds of formula VIII wherein R is hydrogen, $R_2$ is p-nitrobenzyl, $R_4$ is ethyl, $R_6$ is acetyl, X is sulfur and i is zero to obtain the corresponding compound of formula IV wherein $R_5$ is chloro and $R_1$ is as shown in Table IV. IR spectra were measured for solutions in the solvents indicated and NMR spectra were measured for solutions in deuterochloroform.

TABLE IV

| $R_1$ | IR (Microns) | NMR(ppm) |
|---|---|---|
| propyl | 5.6 and 5.78 ($CH_2Cl_2$) | 0.8–1.86(c, 5H); 2.32 and 2.46(s, 3H); 2.62–3.86(c, 4H); 5.3(m, 2H), 5.9 and 6.24(m, 1H); 7.58(m, 2H); and 8.22(m, 2H) |
| 2-(acetyl-amino)ethyl | 5.6, 5.78 and 5.98 ($CH_2Cl_2$) | 1.96(s, 3H); 2.28–3.92(c, 9H); 5.34(m, 2H); 5.92 and 6.12(m, 1H); 6.86(b, 1H); 7.6(m, 2H); and 8.22(m, 2H) |

EXAMPLE 9 p-Nitrobenzyl 2-(2-Ethoxyethylthio-2-penem-3-carboxylate

A solution of 1.1 g p-nitrobenzyl 2-(4-chloro-2-oxo-1-azetidinyl)-3-acetylthio-3-(2-ethoxyethylthio)acrylate in 50 ml methylene chloride and 30 ml water was stirred at 25° C. under a nitrogen atmosphere and with its pH adjusted to 10.5 with an aqueou solution of tetrabutylammonium hydroxide. The pH of the reaction mixture was maintained at 10.5 for 6 hours, then it was adjusted to 5.0 with 1N aqueous hydrochloric acid. The methylene chloride layer was separated, washed with 50 ml water, dried over anhydrous sodium sulfate and concentrated in vacuo. The crude product was purified by chromatography on silica gel, eluting with 10% ethyl acetate in chloroform, to yield 0.3 g of the title compound. The title compound's NMR spectrum in deutrochloroform solution had peaks at 1.16(t,3H); 2.98–4.0(c,8H); 5.3(d,2H); 5.65(m,1H); 7.58(d,2H); and 8.17(d,2H) ppm. The infrared solution in chloroform had an absorption band at 5.57 microns.

EXAMPLE 10

The procedure of Example 9 were used with compounds of formula IV wherein R is hydrogen, $R_2$ is p-nitrobenzyl, $R_5$ is chloro, $R_6$ is acetyl, and X is sulfur to obtain the corresponding compounds of formula I for $R_1$ as shown in Table V. IR spectra were measured for solutions in the solvent indicated and NMR spectra were measured for solutions in deuterochloroform.

TABLE V

| $R_1$ | IR (microns) | NMR(ppm) |
|---|---|---|
| ethyl | 5.57 ($CHCl_3$) | 1.34(m, 3H); 2.36–3.78(c, 4H); 5.3(m, 2H); and 5.66(m, 1H). |
| 3-phenylpropyl | 5.68 ($CHCl_3$) | 2.1(m, 2H); 2.6–3.02(c, 4H); 3.1–4.1(m, 2H); 5.4(d, 2H); 5.72(m, 1H); 7.32(b, 5H); 7.66(d, 2H); and 8.26(d, 2H). |
| methyl | 5.58 ($CHCl_3$) | 2.57(S, 3H); 3.22–4.1(m, 2H); 5.4(d, 2H); 5.78(m, 1H); 7.64 (d, 2H); and 8.28(d, 2H). |
| 2-(acetylamino)ethyl | 5.57 and 6.0 ($CHCl_3$) | 1.96(s, 3H); 2.97–4.0(c, 6H); 5.3(d, 2H); 5.7(m, 1H); 6.2(b, 1H); |

TABLE V-continued

| $R_1$ | IR (microns) | NMR(ppm) |
|---|---|---|
| 2-methoxyethyl | 5.58 (CHCl$_3$) | 7.6(d, 2H); and 8.22(d, 2H). 3.28(s) and 3.0–4.02(c, 9H); 5.3(d, 2H); 5.66(m, 1H); 7–6(d, 2H); and 8.2(d, 2H). |
| propyl | 5.58 (CHCl$_3$) | 1.02(t, 3H); 1.7(m, 2H); 2.95(m, 2H); 3.25–4.05(m, 2H); 5.32(d, 2H); 5.68(m, 1H); 7.6(d, 2H); and 8.24(d, 2H). |
| 2-(4-methyl-thiazol-5-yl)ethyl | 5.58 (CHCl$_3$) | 2.4(S, 3H); 2.9–4.16(c, 6H); 5.34(d, 2H); 5.74(m, 1H); 7.62(d, 2H); 8.24(d, 2H); and 8.64 (S, 1H). |
| 1,3-dioxolan-2-ylmethyl | 5.57 (CHCl$_3$) | 2.9–4.24(c, 8H); 5.0–5.4(c, 3H); 5.64(m, 1H); 7.6(m, 2H); and 8.2 (m, 2H). |
| 2-(2-pyrrolidon-1-yl)ethyl | 5.58 and 5.99 (CHCl$_3$) | 1.74–2.6(c, 4H); 2.83–3.96(c, 8H); 5.2(d, 2H); 5.6(m, 1H); 7.44(d, 2H); and 8.05(d, 2H). |
| 2-(2-furanoylamino)-ethyl | 5.58, 5.77 and 6.06 (CH$_2$Cl$_2$) | 2.77–4.0(m, 6H); 5.3 (d, 2H); 5.6(m, 1H); 6.44(m, 1H); 6.8–7.7(c, 5H); and 8.18 (m, 2H). |
| 2,2-diethoxyethyl | 5.6 (CHCl$_3$) | 1.2(m, 6H); 2.6(m, 2H); 2.8–4.35(c, 7H); 5.32(S, 2H); 5.66(m, 1H); 7.56(d, 2H); and 8.2 (d, 2H). |
| 2-(p-nitrobenzyl-oxycarbonyl-amino)-ethyl | 5.59 and 5.8 (CH$_2$Cl$_2$) | 2.9–4.18(c, 6H); 5.2 (S, 2H); 5.36(S, 2H); 5.73(m, 1H); 7.7(c, 5H); and 8.23(d, 4H). |
| 2-(2-pyridyl)ethyl | 5.57 (CHCl$_3$) | 2.96–4.0(c, 6H); 5.3 (d, 2H); 5.65(m, 1H); 7.12 (m, 2H); 7.6(c, 3H); 8.2 (d, 2H); and 8.5(m, 1H). |

EXAMPLE 11

2-(2-Ethoxyethylthio)-2-penem-3-carboxylic Acid, Calcium Salt

A suspension of 300 mg. of 5% palladium on calcium carbonate in 20 ml water was shaken under an atmosphere of hydrogen at a pressure of ca 55 psi until hydrogen uptake ceased. A solution of 300 mg. of 2-(2-ethoxyethylthio-3-p-nitrobenzyloxycarbonyl-2-penem in 20 ml tetrahydrofuran was added, and this mixture was shaken under an atmosphere of hydrogen at a pressure of ca 55 psi for 1 hour. An additional 0.3 g of 5% palladium on calcium carbonate was added and the hydrogenation continued for an additional 1.5 hours. The catalyst was then removed by filtration and the tetrahydrofuran was removed from the filtrate by evaporation in vacuo. The resulting aqueous solution was washed with ethyl acetate, and then it was lyophilized to give the title compound as an amorphous solid (yield 130 mg). The IR spectrum (KBr disc) showed an absorption at 5.7 microns. The NMR spectrum in perdeuterodimethylsulfoxide showed peaks at 1.1(t,3H); 2.82–3.88(c,8H); and 5.64(m,1H) ppm.

EXAMPLE 12

The compounds of formula I listed in Table V were subjected to hydrogenolysis according to the procedures of Example 11 to obtain the corresponding products of formula I wherein R is hydrogen, R$_2$ is the calcium salt and R$_1$ is as shown in Table VI except in the case of the compound of formula I wherein R$_1$ was 2-(p-nitrobenzyloxycarbonylamino)ethyl which was hydrogenated to yield the 2-aminoethyl derivative with loss of the protective p-nitrobenzyloxycarbonyl group. IR spectra were measured for potassium bromide discs and NMR spectra were measured for solutions in perdeuterodimethylsulfoxide.

TABLE VI

| $R_1$ | IR (microns) | NMR(ppm) |
|---|---|---|
| ethyl | 5.75 | 1.2(m, 3H); 2.36–4.02(c, 4H); and 5.66(m, 1H); |
| 3-phenylpropyl | 5.65 | 1.94(m, 2H); 2.44–2.96(c, 4H); 3.1–3.9 (m, 2H); 5.66(m, 1H); and 7.3(b, 5H). |
| methyl | 5.7 | 2.52(S, 3H); 3.24–3.88 (m, 2H); and 5.66 (m, 1H). |
| 2-(acetylamino)ethyl | 5.65 and 6.1 | 1.82(S, 3H); 1.8–3.88 (c, 6H); 5.64(m, 1H); and 8.32(b, 1H). |
| 2-methoxyethyl | 5.65 | 3.26(s) and 2.86–3.86 (c, 9H); and 5.64(m, 1H). |
| propyl | 5.7 | 0.94(t, 3H); 1.66(m, 2H); 2.76(m, 2H); 3.18–4.0 (m, 2H); and 5.62(m, 1H). |
| 2-(4-methyl-thiazol-5-yl)ethyl | 5.7 | 2.34(S, 3H); 2.96–3.92 (c, 6H); 5.68(m, 1H); and 8.86(S, 1H). |
| 1,3-dioxolan-2-ylmethyl | 5.7 | 2.86–4.0(c, 8H); 5.1 (m, 1H); and 5.6(m, 1H). |
| 2-(2-pyrrdidon-1-yl)ethyl | 5.65 and 6.05 | 1.72–3.88(c, 6H); and 5.64(m, 1H) |
| 2-(2-furanoylamino)ethyl | 5.7 and 6.15 | 2.9–3.92(c, 6H); 5.68 (m, 1H), 6.62(m, 1H); 7.2 (m, 1H); 7.86(m, 1H); and 8.78(m, 1H). |
| 2,2-diethoxyethyl | 5.7 | 1.14(m, 6H); 2.66(m, 2H); 2.86–3.78(c, 7H); and 5.6(m, 1H), |
| 2-aminoethyl | 5.6 | 2.6–3.96(c, 6H); 5.66 (m, 1H); and 7.14(b, 2H). |
| 2-(2-pyridyl)ethyl | 5.7 | 2.86–4.0(c, 6H); 5.65 (m, 1H); 7.26(m, 2H); 7.72(m, 1H); and 8.5 (m, 1H). |

PREPARATION A p-Nitrobenzyl 2-(4-ethylthio-2-oxo-1-azetidinyl)-2-[2-ethoxyethylthio(thiocarbonyl)thio]acetate A solution of 3.58 g potassium 2-ethoxyethyl trithiocarbonate and 3.7 g benzyltriethylammonium chloride in 100 ml methylene chloride was cooled to 0° C. under a nitrogen atmosphere and a solution of 5.3 g of p-nitrobenzyl 2-(4-ethylthio-2-oxo-1-azetidinyl)-2-chloroacetate in 50 ml methylene chloride was added dropwise. The reaction mixture was stirred for 1 hour, then washed with three 50 ml portions of water, dried over anhydrous sodium sulfate and concentrated in vacuo to an oil. (8.6 g). The crude product was chromatographed on silica gel eluting with 5% ethyl acetate in chloroform to yield 2.3 g of the title compound as an oil. The IR spectrum of a chloroform solution of the title compound had an absorption at 5.65 micron; and the NMR spectrum in deuterochloroform showed peeks at 1.2(m,6H);2.34–3.77(c,10H);4.7,4.98(m,1H); 5.26(s,2H); 6.62,6.86(s,1H); 7.43(m,2H); and 8.16(m,2H). ppm.

PREPARATION B

The procedure of Preparation A were employed in reacting compounds of formula V wherein R is hydrogen, $R_2$ is p-nitrobenzyl, $R_4$ is ethyl, $R_7$ is chloro and i is zero with $R_1$ potassium trithiocarbonate to obtain compounds of formula VI. The products are tabulated in Table VII with IR solution spectra measured in chloroform, unless otherwise indicated, and NMR solution spectra measured in deuterochloroform.

TABLE VII

| $R_1$ | IR (microns) | NMR(ppm) |
|---|---|---|
| ethyl | 5.66 | 1.26(m, 6H); 2.4–3.62(c, 6H); 4.7, 5.0 (m, 1H); 5.3(s, 2H); 6.68, 6.92(s, 1H); 7.48 (m, 2H); and 8.2(m, 2H). |
| 3-phenylpropyl | 5.68 | 1.2(m, 3H); 2.02(m, 2H); 2.35–3.6(c, 8H); 4.7 and 4.97(m, 1H); 5.22(s, 2H); 6.6 and 6.87(s, 1H); 7.12 (m, 5H); 7.4(m, 2H), and 8.1(m, 2H). |
| methyl | 5.64 | 1.22(m, 3H); 2.6(m, 2H); 2.8(s, 3H); 3.02–3.88 (m, 2H); 4.78 and 5.02 (m, 1H); 5.34(s, 2H); 6.7 and 6.94(s, 1H); 7.52 (d, 2H); and |
| 2-(acetylamino) ethyl | 5.65 and 5.98 | 1.22(m, 3H); 1.96(s, 3H); 2.62(m, 2H); 3.0–3.72 (c, 6H); 4.8, 5.02(m, 1H); 5.32(S, 2H); 6.36(b, 1H); 6.7 and 6.9(s, 1H); 7.54 (m, 2H); and 8.24(m, 2H). |
| 2-methoxyethyl | 5.67 | 1.24(m, 3H); 2.6(m, 2H); 3.25(s) and 3.0–3.72 (c, 9H); 4.64 and 5.0 (m, 1H); 5.3(s, 2H); 6.9 and 7.22(s, 1H); 7.48(m, 2H) and 8.2(m, 2H). |
| 2-(methyl-thiazol-5-yl)ethyl | 5.65 | 1.26(t, 3H); 2.42(s) and 2.3–3.8(C, 11H); 4.76, 5.0(m, 1H); 5.34(s, 2H); 6.67, 6.93(s, 1H); 7.5 (d, 2H); and 8.2(d, 2H). |
| propyl | 5.66 | 1.16(m, 6H); 1.76(m, 2H); 2.62(m, 2.86–3.86(c, 4H); 4.76 and 5.0(m, 1H); 5.32(s, 2H); 6.7 and 6.9 (s, 1H); 7.46(d, 2H); and 8.2(d, 2H). |
| 1,3-dioxolan-2-ylmethyl | 5.64 | 1.22(m, 3H); 2.17–4.08 (c, 10H); 4.57–5.4(c, 4H); 6.66, 6.9(s, 1H); 7.5 (m, 2H); and 8.22(m, 2H). |
| 2-(2-pyrrolidon-1-yl)ethyl | 5.64 and 6.02 | 1.24(m, 3H); 1.82–3.68 (c, 14H); 4.8, 5.05(m, 1H); 5.35(s, 2H); 6.7, 6.94 (s, 1H); 7.55(m, 2H); and 8.24(m, 2H). |
| 2-(2-furanoylamino)-ethyl | 5.65 and 6.03 (CH$_2$Cl$_2$) | 1.2(m, 3H); 2.24–3.78 (c, 8H); 4.58–5.02(c, 1H); 5.24 (s, 2H); 6.36(m, 1H); 6.57, 6.8(s, 1H); and 6.98 (d, 1H); |
| 2, 2-diethoxyethyl | 5.65 | 1.22(m, 9H); 2.4–4.34 (c, 10H); 4.5–5.4(c, 4H); 6.66, 6.9(m, 1H); 7.5 (m, 2H); and 8.23(m, 2H). |
| 2-(p-nitrobenzyl-oxocarbonylamino)-ethyl | 5.66 and 5.8 | 1.22 (c, 3H); 2.38–3.74 (c, 8H); 4.67–5.4(c, 5H); 6.67, 6.92(s, 1H); 7.53 (c, 5H); and 8.28(m, 4H). |
| 2-(2-pyridyl)ethyl | 5.66 | 1.2(m, 3H); 2.74(m, 2H); 2.9–3.94(c, 6H); 4.66, 4.94 (m, 1H); 5.2(s, 2H); 6.6, 6.83(s, 1H); 7.06(m, 2H); 7.44(c, 3H); 8.14(m, 2H); |

TABLE VII-continued

| $R_1$ | IR (microns) | NMR(ppm) |
|---|---|---|
| | | and 8.45(m, 1H). |

PREPARATION C p-Nitrobenzyl 2-(4-Ethylthio-2-oxo-1-azetidinyl)-2-chloroacetate

To a stirred solution of 6.8 g. of p-nitrobenzyl 2-(4-ethylthio-2-oxo-1-azetidinyl)-2-hydroxyacetate in 200 ml. of tetrahydrofuran at 0°–5° C. was added 2.98 ml. of 2,6-dimethylpyridine. This was followed by dropwise addition of a solution of 1.73 ml. of thionyl chloride in 20 ml. of tetrahydrofuran, over a 5-minute period. Stirring was continued at 0°–5° C. for 15 minutes, and then the reaction mixture was filtered. The filtrate was evaporated to dryness in vacuo, and the residue was dissolved in 200 ml. of dichloromethane. The resulting solution was washed successively with dilute hydrochloric acid and water, and dried with anhydrous sodium sulfate. Evaporation in vacuo gave the title compound as a yellow, viscous liquid (yield: 7.12 g). The IR spectrum (CHCl$_3$) of the product showed an absorption at 5.63 microns. The NMR spectrum (CDCl$_3$) of the product showed absorptions at 1.3(t,3H); 2.47–3.7(m,4H); 4.9–5.3(m,1H); 5.4(s,4H); 6.06 and 6.18(ss,1H); 7.58 (d,2H); and 8.22(d,2H) ppm.

PREPARATION D p-Nitrobenzyl 2-(4-Ethylthio-2-oxo-1-azetidinyl)-2-hydroxyacetate

A solution of 12.3 g. of 4-ethylthio-2-oxo-1-azetidine and 25.5 g. of p-nitrobenzyl glyoxylate ethyl hemiacetal in 900 ml. of benzene was heated under reflux for 16 hours. During the heating for 16 hours, water and ethanol were removed from the reaction mixture by azeotropic distillation using a Dean-Stark trap. At this point, the benzene was removed by evaporation in vacuo, and the residue was dissolved in 700 ml. of dichloromethane. The dichloromethane solution was washed three times with water then dried over anhydrous sodium sulfate. Evaporation in vacuo afforded the title compound as a yellow semi-solid (yield: 32.5 g.). The IR spectrum of the product in chloroform showed an absorption at 5.65 microns. The NMR spectrum of the product in deuterochloroform showed absorptions at 1.25(t,3H); 2.35–3.62(m,4H); 4.3(s,1H); 4.85(m,1H); 5.22 and 5.54 (ss,1H); 5.38(s,2H); 7.5(d,2H); and 8.2(d,2H) ppm.

PREPARATION E

4-Ethylthio-2-oxo-1-azetidine

To a solution of 8.0 g. of sodium hydroxide in 200 ml. of water cooled to 0°–5° C. was added 15.5 ml. of ethanethiol. The cold solution was stirred for 5 minutes, and then a solution of 25.8 g of 4-acetoxy-2-oxo-1-azetidine in 200 ml. of dichloromethane was added in one portion. The mixture was stirred at 0°–5° C. for 90 minutes, and then the pH was adjusted to 6 using 6N hydrochloric acid. The dichloromethane layer was removed, and the aqueous layer was extracted with further quantities of dichloromethane. The combined dichloromethane solutions were washed with water, followed by saturated sodium chloride, and then dried using over anhydrous sodium sulfate. Evaporation in vacuo afforded the title compound as an oil (yield: 23.4 g).

PREPARATION F p-Nitrobenzyl Glyoxylate Ethyl Hemiacetal

A stirred solution of 32.0 g. of the bis(p-nitrobenzyl) ester of tartaric acid in 850 ml. of tetrahydrofuran was cooled to 0°–5° C. and 26.0 g of periodic acid was added all in one portion. Stirring was continued for 2 hours at 0°–5° C. and then the reaction mixture was filtered. To the filtrate was added 100 ml. of ethanol, and then the resulting solution was evaporated in vacuo. The residue was dissolved in 700 ml. of chloroform, and it was washed successively with concentrated aqueous sodium thiosulfate (5 times) and water (2 times). The chloroform solution was dried using anhydrous sodium sulfate and then it was evaporated in vacuo to give the title compound as a viscous liquid (yield: 25.5 g).

PREPARATION G

Potassium 2-ethoxyethyl trithiocarbonate

To a solution of 6.79 g potassium t-butoxide in 300 ml of anhydrous tetrahydrofuran cooled to 0° C. under a nitrogen atmosphere was added 6.42 g of 2-mercaptoethyl ethyl ether. The resulting slurry was stirred at 25° C. for 1 hour, then 4.4 ml. of carbon disulfide was added dropwise at 0° C. The resulting solution was stirred at 25° C. for 30 min., then concentrated in vacuo. Diethyl ether (300 ml) was added and the mixture was filtered, and washed with ether and dried under nitrogen to yield 12.6 g of the title compound as a yellow solid.

Also prepared by this procedure using the appropriate mercaptan starting material were the following potassium trithiocarbonates: 1,3-dioxolan-2-ylmethyl; 2-(p-nitrobenzyloxycarbonylamino)ethyl; 2-(4-methylthiazol-5-yl)-ethyl; 2-(acetylamino)ethyl; 2-(2-pyridyl)ethyl;2,2-diethoxyethyl; 2-(2-furanoylamino)ethyl; and 2-[2-pyrrolidon-1-yl)ethyl.

PREPARATION H

Sodium 2-methoxyethyl trithiocarbonate

To a solution of 1.62 g. sodium methoxide in 75 ml. of anhydrous ethanol cooled to 0° C. under a nitrogen atmosphere was added dropwise a solution of 4.02 g 2-methoxyethylthioacetate in 25 ml of anhydrous ethanol. The solution was stirred at 0° C. for 1 hr. then 2.36 g carbon disulfide was added dropwise. The resulting yellow solution was stirred at 25° C. for 1 hr. then concentrated in vacuo. The residue was triturated with hexane and the hexane was decanted. The residue was then triturated with ether and filtered to yield 3.7 g of the title compound as a yellow solid.

Also prepared by this procedure using the appropriate thioacetate starting material were the following sodium trithiocarbonates: 1,3-dioxolan-2-ylmethyl; 2-(p-nitrobenzyloxycarbonylamino)ethyl; 2-(4-methylthiazol-5-yl)ethyl; 2-(acetylamino)ethyl; 2-(2-pyridyl)ethyl; 2,2-diethoxyethyl; 2-(2-furanoylamino)ethyl; and 2-(2-pyrrolidon-1-yl)ethyl.

I claim:

1. A compound of the formula

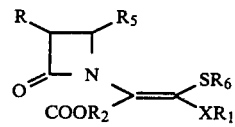

wherein

R is hydrogen, 1-hydroxyalkyl having 1 or 2 carbon atoms or wherein the 1-hydroxyalkyl is substituted with a hydroxyl-protecting group selected from the group consisting of benzyloxycarbonyl, p-nitrobenzyloxycarbonyl, allyloxycarbonyl, 2,2,2-trichloroethoxycarbonyl and trialkylsilyl wherein each alkyl has 1–6 carbon atoms;

$R_1$ is (alk)-G, (alk)-$G_1$, $G_1$ or $CH(G_2)_2$ wherein (alk) is an alkyl group having one to four carbon atoms;

G is hydrogen, alkoxy having one to five carbon atoms, 2-(alkoxy)ethoxy having three to seven carbon atoms, alkylthio having one to five carbon atoms, phenoxy, thiophenoxy, amino, amino substituted with an amine-protecting group wherein said group is benzyloxycarbonyl, p-nitrobenzyloxycarbonyl, allyloxycarbonyl, 2,2,2-trichloroethoxycarbonyl or together with the amine nitrogen being protected azido; N-phenyl-N-alkylamino wherein the alkyl has one to four carbon atoms, N-alkanoylamino having two to six carbon atoms, N-alkoxyalkanoyl)amino having three to ten carbon atoms, 2-(N-alkanoylamino)ethoxy having four to eight carbon atoms, aminocarbonyl, aminocarbonyloxy, N-alkylaminocarbonylamino having two to five carbon atoms, N-alkanoylaminoacetylamino having four to seven carbon atoms, N-alkylaminocarbonyloxy, aminocarbonylalkoxy having two to five carbon atoms, N-alkylaminocarbonyl having two to five carbon atoms, N-(alkoxyalkyl)aminocarbonyl having three to nine carbon atoms;

$G_1$ is azetidinyl or azetidinyl substituted with N-alkanoyl having two to six carbon atoms or an amine-protecting group wherein said group is benzyloxycarbonyl, p-nitrobenzyloxycarbonyl, allyloxycarbonyl, 2,2,2-trichloroethoxycarbonyl or together with the amine nitrogen being protected azido; a five- or six-membered ring which is carbocyclic or heterocyclic having one or two oxygen atoms, one, two, three or four nitrogen atoms, a sulfur atom, a nitrogen atom and an oxygen atom or a nitrogen atom and a sulfur atom, or said five- or six-membered ring substituted with alkyl having one to four carbon atoms, dialkyl each having one to four carbon atoms, oxo, amino, amino substituted with an amine-protecting group wherein said group is benzyloxycarbonyl, p-nitrobenzyloxycarbonyl, allyloxycarbonyl, 2,2,2-trichloroethoxycarbonyl or together with the amine nitrogen being protected azido, alkoxycarbonyl having two to five carbon atoms, di(alkoxycarbonyl) each having two to five carbon atoms, N-alkylamino-carbonyl having two to five carbon atoms, alkoxyalkyl having two to seven carbon atoms, phenyl, formyl, aminocarbonyl, N-alkylaminocarbonylamino having two to five carbon atoms, alkanoylamino having two to five carbon atoms, alkoxy having one to four carbon atoms or phenoxyacetyl; and $G_2$ is alkanoylaminomethyl each having three to seven carbon atoms or alkoxy each having one to four carbon atoms;

$R_2$ is hydrogen, a group which forms an ester which is hydrolyzed in vivo or a carboxylic acid protecting group selected from the group consisting of benzyl, p-nitrobenzyl, allyl and 2,2,2-trichloroethyl;

$R_5$ is chloro, bromo or iodo;

$R_6$ is a sulfur-protecting group selected from alkanoyl having from 2–8 carbon atoms, optionally substituted with alkoxy having from 1–4 carbon atoms, phenyl, pyridyl or 2-benzothiazolyl;

X is oxygen or sulfur; and i is zero or 1.

2. A compound according to claim 1 wherein the amine protecting group is p-nitrobenzyloxycarbonyl or wherein the amine nitrogen to be protected has been converted to an azido group.

3. A compound as in claim 1 wherein R is hydrogen, X is sulfur and $R_1$ is methyl, ethyl, n-propyl, 2-methoxyethyl, 2-ethoxyethyl, 1-methoxy-2-propyl, 2,2-diethoxyethyl, 3-phenylpropyl, 2-(acetylamino)ethyl, 3-tetrahydrofuranyl, 2-tetrahydrofuranylmethyl, 2-(2-furanoylamino)ethyl, 1,3-dioxolan-2-ylmethyl, 2-(2-pyrrolidon-1-yl)ethyl, 2-(4-methylthiazol-5-yl)ethyl, 2-(2-pyridyl)ethyl, 2-aminoethyl or 2-(p-nitrobenzyloxycarbonylamino)-ethyl.

4. A compound in accordance with claim 3 wherein $R_2$ is p-nitrobenzyl.

5. A compound in accordance with claim 1 wherein the group which forms an ester $R_2$ which is readily hydrolyzed in vivo is alkanoyloxymethyl having from 3 to 8 carbon atoms, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-[alkoxycarbonyl]amino)ethyl having from 4 to 10 carbon atoms, 3-phthalidyl, 4-crotonolactonyl, gamma-butyrolacton-4-yl or carboxyalkylcarbonyloxymethyl.

6. A compound in accordance with claim 1 wherein X is sulfur.

7. A compound in accordance with claim 1 wherein $R_6$ is alkanoyl having 2 to 8 carbon atoms or alkanoyl substituted with alkoxy having 1–4 carbon atoms, phenyl, pyridyl or 2-benzothiazolyl.

8. A compound in accordance with claim 7 wherein $R_6$ is alkanoyl having 2 to 8 carbon atoms.

9. A compound in accordance with claim 8 wherein $R_6$ is acetyl.

10. A compound in accordance with claim 1 wherein the hydroxyl-protecting group is p-nitrobenzyloxycarbonyl.

* * * * *